United States Patent [19]
Fisher et al.

[11] Patent Number: 5,053,412
[45] Date of Patent: Oct. 1, 1991

[54] SPIRO NITROGEN-BRIDGED HETEROCYCLIC COMPOUNDS

[75] Inventors: Abraham Fisher, Holon; Ishai Karton, Nes Ziona, both of Israel

[73] Assignee: Israel Institute for Biological Research, Ness Ziona, Israel

[21] Appl. No.: 507,228

[22] Filed: Apr. 10, 1990

[51] Int. Cl.$^5$ .................. A61K 31/445; C07D 498/10
[52] U.S. Cl. ...................................... 514/278; 546/18; 546/19; 546/137
[58] Field of Search ........................... 546/18, 19, 137; 514/278

[56] References Cited

U.S. PATENT DOCUMENTS 3,792,053 2/1974 Potoski et al. ...................... 546/137

FOREIGN PATENT DOCUMENTS 0337547 10/1989 European Pat. Off. ............. 546/18

Primary Examiner—Robert T. Bond
Attorney, Agent, or Firm—Darby & Darby

[57] ABSTRACT

The invention relates to novel compounds (I) for treating diseases of the central and peripheral nervous system:

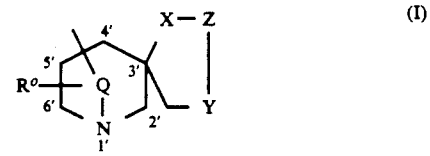

including enantiomers, racemates and acid addition and quaternary salts thereof, wherein one of X and Y is O and the other of X and Y is N; Q is $(CH_2)_n$ or $C(CH_3)_2$ where n is 1, 2 or 3 and the bridge —Q— is attached at one end to position 1 and at the other end to position 4 or 5, and R° is hydrogen, methyl or hydroxyl; in the moiety

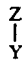

the line connecting Z and Y signifies a double bond when X—Z is O—C—R and Y is N, and a single bond when X—Z is N=C—R and Y is O; Z is C—R wherein R is selected from hydrogen, $NH_2$, NH-R" (R"=$C_{1-6}$-alkyl), N(R")$_2$, R", $C_{2-6}$-alkenyl, $C_{2-6}$-alkynyl, $C_{3-7}$-cycloalkyl, R" substituted by hydroxy or by 1-6 halogen atoms, R"O-$C_{1-6}$-alkyl, carboxy-$C_{1-6}$-alkyl, R"O-CO-$C_{1-6}$-alkyl, amino-$C_{1-6}$-alkyl, R""NH-$C_{1-6}$-alkyl, (R")$_2$N-$C_{1-6}$-alkyl, 2-oxo-pyrrolidin-1-ylmethyl, aryl, diarylmethylol, and R" substituted by one or two aryl groups, wherein aryl denotes phenyl optionally substituted by 1-3 halogens, R", R"O and(or) $CF_3$. Also claimed are compounds wherein the line connecting Z and Y signifies the absence of a bond, X is O, Z is H and Y is $NH_2$, $NO_2$ or $N_3$.

52 Claims, No Drawings

SPIRO NITROGEN-BRIDGED HETEROCYCLIC COMPOUNDS

FIELD OF THE INVENTION

The present invention relates to spiro(1,3-oxazoline-5,3')quinuclidines, spiro(1,3-oxazoline-4,3')quinuclidines, and 3-(substituted methyl)-3-hydroxyquinuclidines and the analogs of these compounds which contain a ring nitrogen-attached bridge of 1-3 carbon atoms; to pharmaceutical compositions containing the spiro compounds and to a method for treating diseases of the central and peripheral nervous system using such spiro-compounds or pharmaceutical compositions.

BACKGROUND OF THE INVENTION

The present applicants were co-inventors of previous patent applications relating to novel spiro-quinuclidine compounds, in which oxathiolane rings were connected in spiro manner with quinuclidine rings, see e.g. European Patent Application No. 0205247 A2, published Dec. 17, 1986, and U.S. Pat. Nos. 4,855,290 (issued Aug. 8, 1989), 4,981,858, (issued Jan. 1, 1991), 4,900,830 (issued Feb. 13, 1990) and 4,876,620 (issued Oct. 24, 1989), the contents of all of which are incorporated herein by reference. These novel compounds were found to possess central nervous system activity. The biological activity of the compound 2-methylspiro(1,3-oxathiolane-5',3)quinuclidine, which exists as geometrical cis- and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of pre-clinical tests that the cis-compound might be especially promising for the control of senile dementia of Alzheimer's type (SDAT). It is also of interest that each of the cis- and trans-isomers may be optically resolved, and the biological activity of the optical isomers was also investigated in a number of cases.

It is a principal object of the invention to provide novel spiro-1,3-oxazoline/bridged-ring compounds, which are distinctive from the aforementioned spiro-oxathiolane/quinuclidine compounds. Further objects of the invention, and especially those which relate to the provision of useful pharmaceutical compositions and methods for the treatment of disease in mammals, will be apparent from the description which follows.

SUMMARY OF INVENTION

The present invention provides novel bridged-ring compounds corresponding with the schematic structural formula (I):

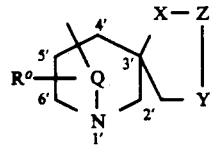

(I)

including enantiomers, racemates and acid addition and quaternary salts thereof, wherein one of X and Y is O and the other of X and Y is N; Q is a member selected from the group consisting of $(CH_2)_n$ and $C(CH_3)_2$ where n is 1, 2 or 3 and the bridge —Q— is attached at one end to position 1' and at the other end to position 4' or 5', and R° is selected from hydrogen, methyl and hydroxyl; and the moiety

denotes a member selected from sub-groups (a) and (b), in which the line connecting Z and Y signifies the presence of a double bond in sub-group (a) when X—Z is O—C—R and Y is N, the presence of a single bond in sub-group (a) when X—Z is N=C—R and Y is O, and the absence of a bond in sub-group (b) and in which: in sub-group (a) Z is C—R wherein R is selected from hydrogen, $NH_2$, $NH$—$C_{1-6}$-alkyl, $N(C_{1-6}$-alkyl$)_2$, $C_{1-6}$-alkyl, $C_{2-6}$-alkenyl, $C_{2-6}$-alkynyl, $C_{3-7}$-cycloalkyl, $C_{1-6}$-alkyl substituted by 1-6 halogen atoms, hydroxy-$C_{1-6}$-alkyl, $C_{1-6}$-alkoxy-$C_{1-6}$-alkyl, carboxy-$C_{1-6}$-alkyl, ($C_{1-6}$-alkoxy)carbonyl-$C_{1-6}$-alkyl, amino-$C_{1-6}$-alkyl, mono-($C_{1-6}$-alkyl)amino-$C_{1-6}$-alkyl, di-($C_{1-6}$-alkyl)amino-$C_{1-6}$-alkyl, 2-oxopyrrolidin-1-ylmethyl, aryl, diarylmethylol, and $C_{1-6}$-alkyl substituted by one or two aryl groups, wherein aryl denotes unsubstituted phenyl or phenyl substituted by 1-3 substituents selected from halogen, $C_{1-6}$-alkyl, $C_{1-6}$-alkoxy and $CF_3$; and in sub-group (b) X is O, Z is H and Y is selected from $NH_2$, $NO_2$ and $N_3$. The present spiro compounds exhibit only optical, but not geometrical isomerism.

Examples of the bridged-ring in formula (I) are:
1-azabicyclo[2,2,2]heptane,
7,7-dimethyl-1-azabicyclo[2,2,1]heptane,
1-azabicyclo[2,2,2]octane (i.e. quinuclidine),
1-azabicyclo[3,2,2]nonane,
1-azabicyclo[3,1,1]heptane,
7,7-dimethyl-1-azabicyclo[3,1,1]heptane,
1-azabicyclo[3,2,1]octane, and
1-azabicyclo[3,3,1]nonane.

Moreover, as indicated by the symbol R° in formula (I), any of these bridged-ring systems may be ring-substituted by methyl or hydroxyl.

These sub-group (a) compounds of the invention, as defined above, have central and peripheral nervous system activity; in such compounds, n is preferably 2, and in a particular embodiment, R may be hydrogen, $NH_2$, $NH$—$C_{1-6}$-alkyl, $N(C_{1-6}$-alkyl$)_2$, $C_{1-6}$-alkyl or aryl. Presently preferred compounds are
2-aminospiro(1,3-oxazoline-5,3')quinuclidine,
2-methylspiro(1,3-oxazoline-5,3')quinclidine,
2-ethylspiro(1,3-oxazoline-5,3')quinuclidine,
2-phenylspiro(1,3-oxazoline-5,3-40 )quinuclidine,
including enantiomers, racemates and acid addition and quaternary salts. thereof.

In the embodiment constituted by sub-group (b), preferred compounds are 3-aminomethylquinuclidin-3-ol, 3-nitromethylquinuclidin-3-ol and 3-azidomethyl-quinuclidin-3-ol. The sub-group (b) compounds are useful intermediates in preparation of group (a) compounds.

The present invention moreover provides pharmaceutical compositions for use in treating diseases of the central and peripheral nervous system in mammals, which comprise an amount effective for use in treating these diseases, of at least one of the spiro-compounds defined by sub-group (a) of the compounds of the invention. Further, the invention provides methods for treating diseases of the central and peripheral nervous system in mammals, which comprise administering to a mammal an amount effective for use in treating these diseases, of at least one of the spiro-compounds defined by sub-group (a) of the compounds of the invention.

DETAILED DESCRIPTION OF THE INVENTION

The above spiro-compounds of formula (I), sub-group (a), may be prepared by reacting the compounds of sub-group (b) with a reactant which will effect formation of the oxazoline ring. Exemplary of sub-group (b), when n=2, is the compound 3-aminomethylquinuclidin-3-ol, which may be prepared either from 3-nitromethylquinuclidin-3-ol, e.g. in the form of the HCl salt, as in Scheme A, or from 3-azidomethylquinuclidin-3-ol as in Scheme B. These nitro and azido compounds are also included in the invention.

Scheme A

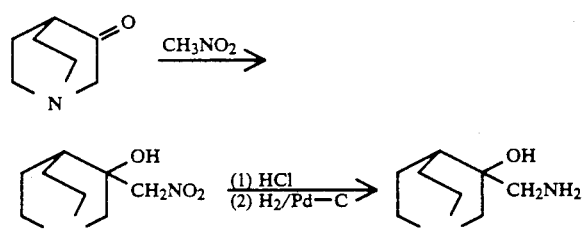

Scheme B

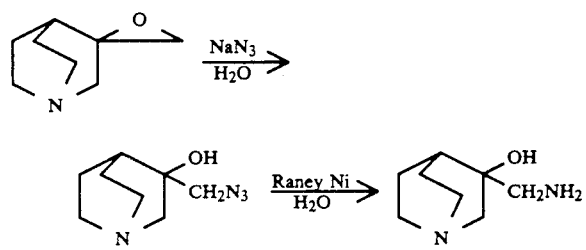

It should be noted that in Scheme B, reaction of sodium azide with the epoxide of 3-methylenequinuclidine in aqueous solution resulted in formation of a single product, 3-azidomethylquinuclidin-3-ol; addition to the latter of wet active Raney Nickel until the evolution of nitrogen ceased resulted in the formation of the desired compound. The major advantages of the Scheme B approach are:

a) there is no need to isolate any intermediates; and b) no hydrogenation apparatus is needed since the hydrogen content of the catalyst is sufficient.

It has now surprisingly been found that the 3-aminomethyl product of either of these reaction schemes may be readily condensed with a carboxylic acid RCOOH to give the spiro-products, whereas it was previously believed that formation of the oxazoline ring by condensation of amino-alcohol and carboxylic acid would proceed smoothly only when the amino-alcohol is completely substituted on the carbon atom to which the NH$_2$ group is connected [see "Oxazolines, their Preparation, Reactions and Applications", J. A. Frunp, Chem. Rev. 71, 483–505 (1971)]. The corresponding imidate RC(:NH)—O—alkyl can be alternatively used, in place of the carboxylic acid RCOOH. The reactions affording compounds of formula I when the bridged-ring is, e.g., quinuclidine, may be represented as follows:

Scheme C

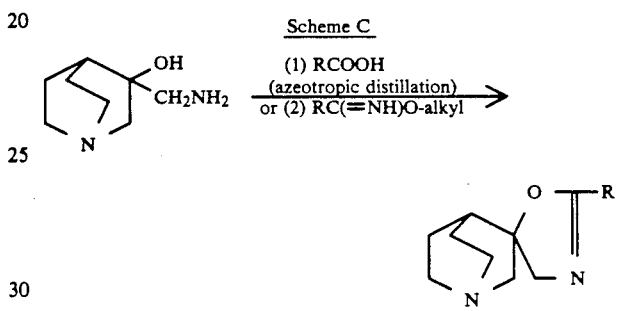

In order to obtain the spiro-quinuclidine compound, for example, when n=2 and R=NH$_2$, it is however preferred to react cyanogen bromide with 3-aminomethylquinuclidin-3-ol.

It will be appreciated that while the foregoing methods will be effective to prepare those sub-group (a) compounds of the invention in which X is O and Y is N, in order to apply similar methods for the purpose of preparing the corresponding sub-group (a) compounds of the invention in which X is N and Y is O, a suitable starting material would be (illustratively, where the ring spiro-connected to oxazoline is quinuclidine) 3-amino-3-hydroxymethylquinuclidine. This starting material may be prepared, e.g., according to Scheme D:

Scheme D

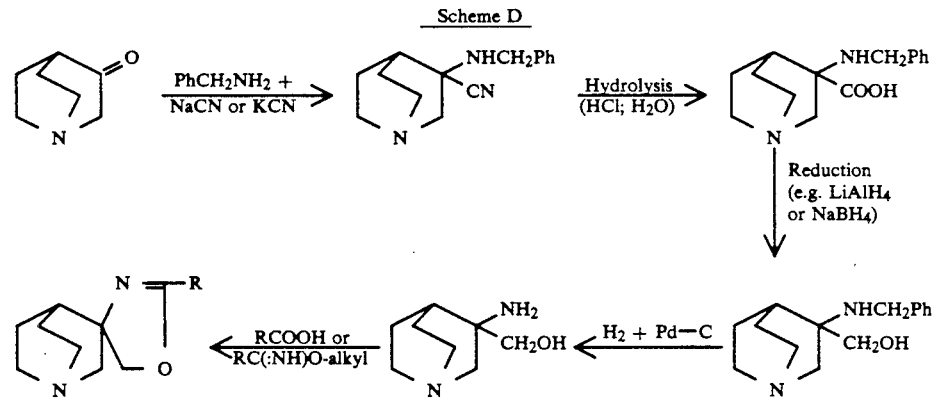

As already mentioned, the spiro-compounds of the invention (as also the sub-group (b) compounds) exhibit optical activity; the racemates can be resolved by use of optically active acids such as dibenzoyl-L- or D-tartaric acid, ditolyl-L- or D-tartaric acid.

At least those spiro-compounds of the present invention where R is methyl or amino are centrally active muscarinic agonists. Due to their pharmacological properties, these compounds can activate central cholinergic functions under conditions where the cholinergic system is hypofunctional.

The spiro-compounds of the invention are in general potentially useful for the treatment of presenile and senile dementia, senile dementia of Alzheimer's type (SDAT), atypical Alzheimer's disease (Perry et al, Advances in Neurology, eds. R. J. Wurtman et al., 51:41, 1990), combined multiinfract dementia and Alzheimer's disease, age-associated memory impairments (AAMI), acute confusion disorders, emotional and attention disorders, mania, tardive-dyskinesia, hyperkinesia, mixed Alzheimer's and Parkinson's disease, aphasia, hallucinatory-paranoid states, post encephalitic amnesic syndrome, alcohol withdrawl symptoms, Huntington's chorea, Pick's disease, Friedrick's ataxia, Gilles de la Tourette disease and Down syndrome, because all of these disease states are disturbances in which a central cholinergic hypofunction has been implicated at least to a certain extent. The spiro-compounds of this invention are also potentially analgesic agents and therefore may be useful in the treatment of severe painful conditions such as rheumatism, arthritis and terminal illness. The spiro-compounds of the invention in which R is methyl, amino, ethyl, would appear to be of particular potential value for the treatment of SDAT and related disorders.

The spiro-compounds of the present invention may be used in combination with acetylcholinesterase inhibitors such as physostigmine or tetrahydroaminoacridine; in combination with acetylcholine precursors such as choline or lecithin; in addition to "nootropic" drugs such as piracetam, aniracetam, oxiracetam, or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin; in combination with a peripheral autimuscarinic agent (such as pirenzepine, N-methyl atropine, N-butylscopolamine, propantheline, methantheline, glycopyrrolate, or tropenzilium) to counteract peripheral adverse effects that might be expected at high doses, such as salivation, diarrhea, gastric secretion or vomiting, or in combination with transdermal scopolamine such as Scopoderm ® to counteract nausea and/or vomiting; in combination with antidepressants such as nortriptyline, amitriptyline, imipramine, minaprine in order to alleviate both the cognitive impairments and depressive symptoms associated sometimes with SDAT, AAMI, mixed SDAT/Parkinson's disease (PD); in combination with M2-antimuscarinic drugs such as secoverine, AFDX-116 (c.f. Hammer et al, 1986 Life Sci. 38:1653) in order to counteract peripheral adverse side effects that might be expected at high doses of the compounds, to counteract inhibitory effects of such agonists at central inhibitory presynaptic and postsynaptic receptors of M2 type and to potentiate the release of acetylcholine via inhibition of inhibitory autoreceptors of M2 type at intact terminals; in combination with nicotinic agonists such as nicotine in order to stimulate both the nicotinic and muscarinic receptors in the brain; in combination with an adrenergic agonist (clonidine or quanfamicine) in order to alleviate both the cognitive and other impairments associated with a mixed cholinergic-noradrenergic deficiency in SDAT; in combination with inhibitors of neuronal serotonin reuptake such as alaproclate, zimelidine in order to alleviate both the cognitive and other emotional functions in SDAT; in combination with monoamine oxidate-B inhibitors like deprenyl in order to alleviate both cognitive and other motor impairments associated with mixed states such as SDAT/PD; in combination with Nerve Growth Factor (NGF, which is administered either by a nasal spray or intracerebroventricularly).

The spiro-compounds of the present invention, with or without the aforementioned other active substances, can be administered for example, by way of injection in a suitable diluent or carrier, per os, rectally in the form of suppositories, by way of insufflation or nasal spray, by infusion or transdermally in a suitable vehicle with or without physostigmine or tetrahydroaminoacridine, for example by using the device which is the subject of U.S. Pat. No. 2,163,347 (issued Nov. 29, 1988).

The present spiro-compounds, especially where R=methyl or $NH_2$, are also of potential use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyrylcholinesterase, and may also be used for the treatment of peripheral cholinergic disorders such as myasthenia gravis, urinary bladder dysfunctions, Adi's disease and Eaton-Lambert disease. These compounds might also be used in disturbances where cholinergic underactivity is induced by drugs.

The present spiro-compounds, especially where R is ethyl, or up to $C_6$-alkyl or aryl, are anticholinergic agents and may potentially be used for treatment of disorders due to a cholinergic hyperfunction, whether this be spontaneous or drug-induced. These compounds are of potential use in the treatment of various diseases such as PD, pseudo-PD, mixed AD/PD, primary dystonias, spasmodic torticollis, cranial dystonia, depression, motion sickness, akathisia (after neuroleptic withdrawal), central hypertension, human head injury, mixed tardive dyskinesia and PD, manic-depression, as adjuncts in surgery instead of atropine, scopolamine, etc., in intoxication due to an excess of acetylcholine like inhibition of acetylcholinesterase. These may also be used in ophthalmology when either prolonged or short-term mydriasis is required.

The present spiro-compounds may also potentially be used in the treatment of disease characterized by excess peripheral-like activity such as asthma, chronic obstructive pulmonary disease, peptic ulcer disease. For these peripheral disorders it is recommended to use the quaternary salts of the formula (Ia) or (Ib)

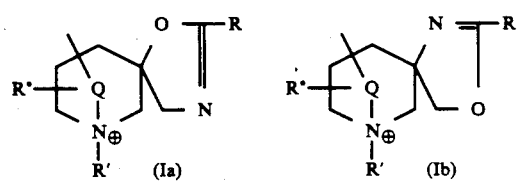

where the tertiary nitrogen is quaternized by R', where this is, e.g., lower ($C_{1-6}$) alkyl, aryl such as phenyl, or aryl-substituted $C_{1-6}$ alkyl such as benzyl.

The invention will now be illustrated by the following non-limiting Examples.

EXAMPLE 1

2-Methyl-spiro(1,3 oxazoline-5,3')quinuclidine (a) 3-Nitromethylquinuclidin-3-ol Quinuclidin-3-one (125 g., 1 mole) was dried by azeotropic distillation (40% w/w in toluene) and placed in a 3 l. flask equipped with a mechanical stirrer, 1 l. methanolic sodium ethoxide was added and the clear solution was stirred at 15°-20° C. Nitromethane, 61 g. (1.0 mole), dissolved in 500 ml. absolute ethanol was then added over 0.5 hour while keeping the temperature below 20° C. The solution was acidified to pH=1 using HCl-isopropanol, filtered and dried to yield 160 g. crude product which was used as such for the next step.

$^1$H-NMR (D$_2$O, DSS) (HCl salt): δ 3.79 (d as part of an AB-type spectrum, one H of CH$_2$NO$_2$), 3.38-3.33 (m, 7H), 2.36 (m, 1H), 2.36-1.95 (m, 4H)

(b) 3-Aminomethylquinuclidin-3-ol (i) By reduction of 3-nitromethylquinuclidin-3-ol A solution of 3-nitromethylquinuclidin-3-ol hydrochloride in methanol was reduced by catalytic hydrogenation using 10% Pd on activated carbon to yield the HCl salt of 3-aminomethylquinuclidin-3-ol, which was recrystallized from methanol-isopropanol to give the product as white crystals.

(ii) Via the azide

3-Methylenequinuclidine epoxide (25 g., 0.18 mole) and sodium azide (20 g., 0.3 mole) were dissolved in 50 ml. water. The mixture was stirred overnight at room temperature, extracted with chloroform (2×200 ml.) and the extracts were concentrated by evaporation. The oily residue containing 3-azidomethylquinuclidin-3-ol was dissolved in water and wet active Raney nickel was added in portions with stirring until the evolution of nitrogen ceased (35 g.). The mixture was filtered, the filtrate was concentrated by evaporation and the residue was recrystallized from isopropanol to yield 9 g. pure 3-aminomethylquinuclidin-3-ol.

MS M+ 156, base peak m/e 139 (M—NH$_3$), and m/e 96 which is typical of the quinuclidine skeleton.

$^1$H NMR (D$_2$O, DSS) (free base): δ 1.3-2.0(5H); 2.3-3(8H). (di-HCl salt): δ 1.8-2.4(m,5H); 3.2-3.5(m,8H).

The $^1$H-NMR of the dihydrochloride salt in comparison to the free base shows a downfield shift of six hydrogens attached to carbons adjacent to the nitrogens (e.g. δ 2.5-2.9 to 3.3-3.5 ppm) in accordance with the expected structure.

(c) 2-Methyl-spiro(1,3 oxazoline-5,3')quinuclidine (AF125)

(i) Ethyl acetamidate method

3-Aminomethylquinuclidin-3-ol (9.1 g., 0.058 mole) was dissolved in 500 ml. dichloromethane; ethyl acetamidate-HCl salt (14 g., 0.11 mole) was added and the mixture was stirred at 5° C. for six hours. The solution was made alkaline with Dowex 1, filtered and the solvent was evaporated to yield an oily residue, which was distilled at 60°-65° C./0.5 mm. Hg to yield AF125 as a colorless liquid.

MS (M+)181 base peak, 139 (M-CH$_3$CN).

$^1$H-NMR (CDCl$_3$-TMS): δ 1.97(dd,3H)(J=1.3 Hz); 2.8-2.9(m,1H); 3.14(d,1H)(J=12 Hz); 3.5(dd,1H)(J=13 Hz), 1.3 Hz); 3.96(dd,1H)(J=13 Hz, 1.3 Hz).

$^1$H-NMR including spin decoupling experiments enable the assignment of the hydrogens adjacent to C$_2$, C$_9$ and the methyl group. Each of the hydrogens adjacent to C$_9$ shows a double doublet (J=13 Hz geminal coupling) and a homo-allylic coupling with the methyl group (J=1.3 Hz). Irradiation at 1.97 (methyl group) brings about the disappearance of the homo-allylic coupling at 3.5 and 3.9 ppm and vice versa. Irradiation at 3.5 effects the signal at 3.96 and vice versa which must be due to geminal coupling of H$_{9a}$ and H$_{9b}$ (Table 1). The $^{13}$C-NMR spectrum (in CDCl$_3$) is very informative and enables the assignment of most resonances to the appropriate carbons.

$^{13}$C-NMR (CDCl$_3$-TMS): δ 13.2(CH$_3$); 20.5 (CH$_2$CH); 21.5(CH$_2$CH); 30.0 (CHCH$_2$); 45.3, 45.7(CH$_2$CH$_2$N); 62.2, 64.2(CH$_2$N); 84.0(COCH$_2$); 165(GCH$_3$).

TABLE 1

$^1$H-NMR SPECTRA OF (+)AF125

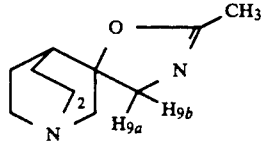

| Solvent | Irradiation ppm | H$_{2a}$ | H$_{2a}$ | H$_{9a}$ | H$_{9b}$ | CH$_3$ |
| --- | --- | --- | --- | --- | --- | --- |
| CDCl3 | — | 3.14 d(J=12Hz) | 2.8-2.9 m | 3.50 dd(J=13, 1.3Hz) | 3.96 dd(J=13, 1.3Hz) | 1.97 dd(J=1.3Hz) |
| C D | — | 3.10 d(J=12Hz) | 2.6 d(J=12Hz) | 3.35 dd(J=13, 1.3Hz) | 3.75 dd(J=13, 1.3Hz) | 1.73 dd(J=1.3Hz) |
| CDCl3 | 3.53 | n.e | n.e | — | 3.96 s | 1.97 d |
|  | 3.96 | n.e | n.e | 3.50 s | — | 1.97 d |
|  | 1.97 | n.e | n.e | 3.50 d(J=13Hz) | 3.96 d(J=13Hz) | — | n.e. not effected

GC (one peak): column 25 m., diameter, 0.2 mm., packing, 5% phenyl methyl silicone; detector type, FID; temperature: column, 125° C., injection port, 220° C., detector, 220° C., carrier gas: N$_2$, 0.7 ml./min.; retention time 6.2 min.

(ii) Acetic acid method

3-Aminomethylquinuclidin-3-ol (10 g.) was dissolved in acetic acid (50 ml.), azeotropicaly distilled in xylene for 30 hours, and the solution was cooled and was made alkaline with cold aqueous potassium carbonate. The organic phase was dried and evaporated to yield 5.2 g. crude product which was distilled under reduced pressure (60°-65° C./0.5 mm. Hg to yield a colorless liquid which solidified under refrigeration. The compound obtained was identical to AF125 obtained by method (c) (i).

d) Optical resolution of AF125

(Preliminary note: owing to the possibility that the polarimeter used to determine the optical rotation data may not have been re:ble, the purity of the optical isomers was evaluated using $^1$H-NMR, as described below.)

To a stirred cold solution of AF125 (15.5 g., 0.085M) in acetone (150 ml.) there was added dropwise a solution of dibenzoyl-L-tartaric acid (18.8 g., 0.05M). A crystalline material separated immediately. The precipitated salt was collected and purified by dissolving in hot isopropanol, cooling and adding ether to the cold solution until turbid precipitating; one repetition of this procedure gave a product of constant optical rotation $[\alpha]_D^{20} = -28°$(MeOH); m.p. 145°.

In a similar manner, the corresponding salt of the other enantiomer was obtained, starting from AF125 (14.74 g., 0.08M) and dibenzoyl-D-tartaric acid (17.76 g., 0.047M) of the corresponding tartaric acid. After 3 crystallizations, the product had $[\alpha]_D^{20} = +26°$-(MeOH); m.p. 145°.

The respective free bases were obtained by neutralization of the salts with a 10% solution of $K_2CO_3$ and several extractions with chloroform. The free base derived from the salt of dibenzoyl-D-tartaric acid) had $[\alpha]_D^{20} = -43°$(MeOH), while that derived from the salt of dibenzoyl-L-tartaric acid had $[\alpha]_D^{20} = +36°$(MeOH).

As indicated above, the optical purity of the enantiomers was shown by $^1$H-NMR. Thus the $^1$H-NMR spectrum of AF125 as a racemate in the presence of optically pure resolving agent (s)(+)2,2,2 trifluoro-1-(9-anthryl)-ethanol reveals two optical isomers. The difference in chemical shift (in $C_6D_6$) of one of the hydrogens which is attached to $C_2$ enables determination of the optical purity of AF125. Each separated enantiomer reveals only one doublet (half an AB-type spectrum) for one of these hydrogens on $C_2$.

EXAMPLE 2

2-Ethyl spiro(1,3 oxazoline 5,3')quinuclidine (AF123)

Similarly to Example 1(c), the title product was obtained by condensation of 3-aminomethylquinuclidin-3ol with propanoic acid followed by azeotropic distillation in xylene. Purification of crude AF123 was effected by vacuum distillation under reduced pressure.

MS: M 195, base peak.

$^1$H-NMR (CDCl$_3$-TMS): $\delta$ 4.0(d,1H)(J=13 Hz); 3.55(d,1H)(J=13 Hz); 3.1(d,1H); 2.7–2.9(m); 2.3(q,2H)(J=7.5 Hz, CH$_2$CH$_3$); 1.1(t,3H)(J=7.5 Hz,CH$_3$).

GC (same conditions as for AF125; one peak): retention time, 8.86 min.

EXAMPLE 3

2-Amino-spiro(1,3-oxazoline-5,3')quinuclidine AF125(N)

The amino-oxazoline derivative AF125(N) is an example of an electron rich oxazoline ring, since the amino nitrogen is conjugated to the double bond, enhancing the negative charge on the imino nitrogen.

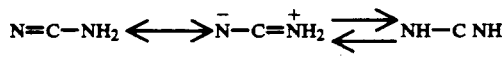

3-Aminomethylquinuclidin-3ol (6g.) and cyanogen bromide (3.5 g.) were dissolved in methanol (200 ml.). The reaction mixture was stirred at room temperature for 5 hours, and then concentrated under vacuum. The residue was purified on an alumina column (300 g.), using a multisystem solvent as an eluent (1.5:1.0:0.2:0.06 CHCl$_3$/ether/methanol/NH$_4$OH). An almost pure fraction of 450 mg. as obtained, which was finally purified by trituration with acetone to give a pure crystalline material. The first chromatographic separation gave also various products including 2 g. of crude desired product which was subjected to a further separation on a column of silica, using as eluent 2% NH$_3$ in methanol. The pure product has a m.p. 135°–136°.

$^1$H-NMR (CDCl$_3$-TMS): $\delta$ 3.83, 3.43, 3.2 (3 doublets, 3H, Hb and Hc, J=0.048 Hz); (m,5H); 1.9 (b, 2H); 1.5 (m, 3).

FAB-MS showed a molecular ion (M+1) 182.

EXAMPLE 4

2-Phenyl-spiro(1,3oxazoline-5,3')quinuclidine AF125(Ph)

A suspension of 3-aminomethylquinuclidin-3-ol (2 g., 0.01 mole) and ethyl imidobenzoate hydrochloride (2 g., 0.01 mole) in ethanol (200 ml.) was mixed for 24 hours at room temperature. After filtration and concentration of the filtrate by evaporation, the crude residue was basified with NaHCO$_3$ and extracted with dichloromethane. The organic extracts were concentrated by evaporation and the crude residue was separated on an alumina column (30 g., 1.5 cm. diameter) using a multisolvent 91.0:1.0:0.2:0.026 CHCl$_3$/ether/methanol/ 32% aq. NH$_4$OH as eluent. The product was rapidly eluted (after 40 ml). The solvent was evaporated without heating and a white solid was obtained, m.p. 65°–70° C.

$^1$H-NMR(CDCl$_3$): $\delta$ 7.955 (2H), 7.72 (2H), 4.16 (d,1H, 3.73 (d, 1H), 3.26 (d, 1H), 2,93 (d, 1H) and (t, 2H), 2.77 (t, 2H), 2.2 (m, 1H), 1.95 (m, 1H), 1.60–1.52 (m, 3H) ppm.

IR (CHCl$_3$) 2920, 2900, 2850sh, 1640sh, 1630, 1625sh, 1440, 1337, 1265, 1250, 1070, 1050, 1035, 1005, 965 cm$^{-1}$.

Mass Spectrum: m/e 242 (60% [M+], 198 (30%, 171 (12%), 149 (10%, 139 (50%0, 124 (17%, 122 (20%, 121 (20%), 117 (30), 111 (12%), 105 (33%), 96 (100%), 82 (50%), 69 (42%), 55 (36%).

CHEMICAL AND PHYSICAL PROPERTIES OF THE OXAZOLINE DERIVATIVES

Most of the spiro-exazoline compounds are relatively stable. AF125, for example, is thermally stable and can be distilled at 130° without decomposition. Its chemical behaviour resembles that of known 2-oxazoline derivatives. In aqueous solution the free base shows a slight decomposition after a few hours which increases gradually with time. The formation of the decomposition products can be monitored with $^1$H-NMR by inspection at two regions $\delta$ 3.3–3.5 (appearance of two doublets) and 1.9–2.0 ppm (appearance of two additional singlets).

The expected decomposition pattern (when e.g., X is O and Y is N) involves opening of the oxazoline ring to form both amide and ester as shown in Scheme E, in which the quinuclidine-derived compounds are depicted illustratively. The formation of two new singlets at $\delta$ 1.9–2.0 ppm as expected for R=Me of these two structures are in agreement with this supposition.

Scheme E

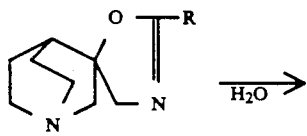

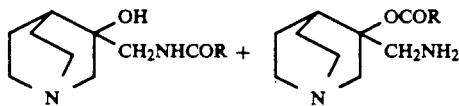

The same pattern of decomposition can be shown for R=Et (AF123). Ring opening is much faster in the presence of dilute hydrochloric acid. It is noted that heating of the tartrate and mandelate salts in tetrahydrofuran also resulted in partial decomposition. The tendency to decomposition of such salts complicates the optical separation of compounds such as AF125 and AF123. However, this problem can be overcome by using the method described for the optical separation of the enantiomers of AF125, or alternatively the aminoalcohols such as 3-aminomethylquinuclidin-3-ol can be resolved and the separated enantiomers can then be cyclized using an ester or imidate as already described. In yet another alternative the N-acyl derivatives of (e.g.) 3-aminomethylquinuclidin-3-ol can be resolved and the separated enantiomers can then be cyclized per se as shown in Scheme F:

Scheme F

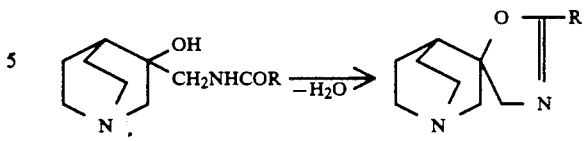

For this cyclization, there may be used, e.g., p-toluene sulfonic acid, or boron trifluoride etherate.

BIOLOGICAL TESTING

Test 1

For an investigation of the potency of AF125, AF123, AF125(N) and AF125(Ph) (and for comparison other putative cholinergic compounds) in displacing from rat brain homogenates, frontal cortex or cerebellum, there were used the following $^3$H-labelled compounds, namely, (31)$^3$H-quinuclidinyl benzilate ($^3$H-QNB; a non-selective M1 and M2 antagonist) and $^3$H-Pirenzepine ($^3$H-PZ; a selective M1 antagonist). For comparison purposes, oxotremorine (an M2 tertiary agonist), carbachol (CCh; an M2 quaternary agonist), AF102B (an M1 tertiary agonist; see U.S. Pat. No. 4,855,290) and McN-A-343 (an M1 quaternary agonist) were included. The results are shown in Tables 2 and 3.

TABLE 2

Apparent affinity states for M1 (displacement of $^3$H-PZ from rat cerebral cortex) and for M2 muscarinic receptors (displacement of $^3$H-QNB from rat cerebellum)

| | CORTEX | | | | CEREBELLUM | | | | | | |
|---|---|---|---|---|---|---|---|---|---|---|---|
| | $^3$H-PZ-Binding | | | | $^3$H-QNB-Binding | | | | | | |
| COMPD. # | $K_H$ (a) µM | $K_L$ (b) | % H | L | $K_H$ (c) µM | $K_L$ (d) | % H | L | RATIOS c:a | d:b | b:a |
| 2 | 0.1 | 6.7 | 53 | 47 | 0.069 | 5.2 | 49 | 51 | 0.69 | 0.78 | 67 |
| 3 | | | | | 0.014 | 0.58 | 35 | 65 | | | |
| 4 | 1 | * | 100 | * | 6 | * | 100 | * | 6 | * | * |
| 5 | 0.035 | 17 | 16 | 84 | 2.3 | 21 | 67 | 33 | 65.7 | 1.23 | 486 |
| 7 | 0.6 | 3 | 28 | 72 | 5.0 | * | 100 | * | 83 | | |
| 8 | 1.3 | * | 100 | | 3.9 | * | 100 | * | 3.0 | * | * |
| 9 | 0.08 | * | 100 | * | 1.37 | * | 100 | * | 17.1 | * | * |
| 10 | 1.54 | * | 100 | * | 11 | * | 100 | * | 7.3 | * | * |

TABLE 3

Apparent affinity states for M1 (displacement of $^3$H-QNB from rat cerebral cortex) and for M2 muscarinic receptors (displacement of $^3$H-QNB from rat cerebellum)

| | CORTEX | | | | CEREBELLUM | | | | | | | |
|---|---|---|---|---|---|---|---|---|---|---|---|---|
| | $^3$H-PZ-Binding | | | | $^3$H-QNB-Binding | | | | | | | |
| COMPD. # | $K_{H1}$ (a) µM | $K_{L1}$ (b) | % H1 | L1 | $K_{H2}$ (c) µM | $K_{L2}$ (d) | % H2 | L2 | RATIOS c:a | d:b | b:a | d:c |
| 1 | 0.6 | 235 | 28 | 72 | 0.75 | 50 | 61 | 39 | 1.25 | 0.21 | 392 | 67 |
| 2 | 0.11 | 37 | 26 | 74 | 0.069 | 5.2 | 49 | 51 | 0.63 | 0.14 | 336 | 75 |
| 3 | 0.016 | 1.6 | 13 | 87 | 0.014 | 0.58 | 35 | 65 | 0.88 | 0.36 | 100 | 41 |
| 4 | 1.8 | * | 100 | * | 5.9 | * | 100 | * | 3.28 | * | * | * |
| 5 | 4.1 | 79 | 66 | 34 | 2.3 | 21 | 67 | 33 | 0.56 | 0.27 | 19.1 | 9.1 |
| 7 | 112 | * | 100 | * | 50 | * | 100 | * | 0.4 | * | * | * |
| 9 | 0.8 | * | 100 | * | 1.37 | * | 100 | * | 1.7 | * | * | * |
| 10 | 5.84 | * | 100 | * | 11 | * | 100 | * | 1.9 | * | * | * |

*Competition curves were significantly better fitted to an one site-model (mass-action curve).

The K values were generated by a non-linear, least-squares curve fitting of the data using the GRAPH-PAD-2 2- and 1- site analysis and statistics.

From Tables 2 and 3, it is evident that the present spiro-compounds show a preference for subtypes of muscarinic receptors, in particular of the M1 type.

KEY TO COMPOUNDS IN TABLES (1) Carbachol
(2) Oxotremorine-M
(3) Oxotremorine
(4) AF102B
(5) AF125
(7) AF125(N)
(8) AF123
(9) AF125(Ph)
(10) McN-A-343

TEST 2

Experiments with the guinea-pig ileum preparation

All the newly synthesized compounds were tested for their agonistic and antagonistic activities in the guinea-pig ileum preparation. Table 4 summarizes qualitatively the results obtained with the tested compounds. As can be seen from Table 4, the most potent agonist among the AF125. AF125 was found to be a full agonist in the guinea-pig ileum preparation and its $EC_{50}$ was calculated as 1.3 μM. The $EPMR_{ACh}$ of AF125 was about 14 as compared to values ranging between 50–100 which are found for AF102B. This compound showed also high affinity toward muscarinic binding sites in the brain. In fact, comparison between AF102B and AF125 showed that AF125 is more active by an order of magnitude than AF102B in its ability to contract the guinea-pig ileum. Thus, AF125 induced much greater contractile response than AF102B at the same concentration

TABLE 4

The effect of various putative cholinergic compounds on the guinea-pig ileum preparation

| Tested compd. | Lowest conc. (μM) | ♦ | Highest conc. (μM) | ♦ | Remarks |
|---|---|---|---|---|---|
| AF123 | 66 | — | 660.0 | — | Blocked reversibility ACh-induced contractions |
| AF125 | 0.2 | + | 1.7 | +++ | Full agonist; contractions were blocked by atropine |
| AF125(N) | 16.6 | + | 133.0 | +++ | Full agonist; contractions |

TABLE 4-continued

The effect of various putative cholinergic compounds on the guinea-pig ileum preparation

| Tested compd. | Lowest conc. (μM) | ♦ | Highest conc. (μM) | ♦ | Remarks |
|---|---|---|---|---|---|
| AF125(Ph) | 0.1 | — | 10 | — | were blocked by atropine Antagonist $IC_{50} = 0.9$ μM |

♦ intensity of contractions

The response is qualitatively described by the number of the plus signs, where + relates to a small contractile response and +++ relates to an intense one. No contractile response is marked by a — sign.

The amino analogue of AF125, [AF125(N)] was also active as an agonist, but higher concentrations of this compound were needed to contract the ileum. As can be seen, AF125(N) is active only at concentrations which are higher by one order of magnitude as compared to AF102B. In spite of its weak agonistic properties, as judged from this test, such compound may still be suitable for the treatment of Alzheimer's disease. AF125(Ph) is an antagonist ($IC_{50} = 0.7$ μM). In contrast to the amino analogue of AF125 and AF123 was found to be an antagonist.

TEST 3

GENERAL PHARMACOLOGICAL AND TOXICITY PROFILE

Male white mice of the CD-1 strain (Charles River, UK), within the body weight range of 18–26 g, were used throughout the study.

AF125

Dose-range finding trials with AF125 injected i.p. into mice at dose levels ranging from 50 to 200 mg./kg., indicated that the toxic-lethal dose falls within the 100 to 200 mg./kg. range. Furthermore, these initial trials clearly established that the major signs of reactions to treatment consisted primarily of signs characteristic for potential cholinomimetic activity of the test material, such as tremors, salivation, lacrimation, diarrhea, analgesia, hypothermia and vasodilation. Survivors exhibited initial signs of recovery at about 2 to 3 hours post-injection. Results following p.os and i.v. injection of AF125 at non-lethal doses are listed in the following Table 5.

TABLE 5

| Dose mg/kg | Route of Admin | Tre | Con | Res | Sal | Lac | Dia | Ana | Myd | Mot | Pil | Hyp |
|---|---|---|---|---|---|---|---|---|---|---|---|---|
| 40 | i.v. | 5/5 | 1/5 | 3/5 | sev | sev | mod | 5/5 | mod | dec | mod | mod |
| 20 | i.v. | 2/5 | 0/5 | 1/5 | sev | sev | mod | 5/5 | mod | dec | mod | mod |
| 10 | i.v. | 0/5 | 0/5 | 0/5 | mod | sli | sli | 5/5 | sli | dec | sli | sli |
| 5 | i.v. | 0/5 | 0/5 | 0/5 | sli | sli |  | 5/5 | sli | dec |  |  |
| 50 | p.os | 2/5 | 0/5 | 0/5 | mod | mod | sli | 5/5 | sli | dec | mod | sli |
| 40 | p.os | 0/5 | 0/5 | 0/5 | sli | mod | sli | 3/5 |  | dec | sli | sli |
| 20 | p.os | 0/5 | 0/5 | 0/5 | sli | sli |  | 0/5 |  |  |  |  |

*Major Signs Observed

TABLE 5-continued

| Dose mg/kg | Route of Admin | Major Signs Observed* | | | | | | | | | |
|---|---|---|---|---|---|---|---|---|---|---|---|
| | | Tre | Con | Res | Sal | Lac | Dia | Ana | Myd | Mot | Pil | Hyp |
| 10 | p.os | 0/5 | 0/5 | 0/5 | | | | | | | | |

*Numberical values of data presented refer to no. of animals affected out of the total no. of animals treated. For other abbreviations see details below:
Tre = Tremors
Con = Convulsive seizure, mostly of the clonic-tonic type
Res = Respiratory distress, mostly hyperpnoea and tachypnoea
Sal = Salivation: sli = slight; mod = moderate; sev = severe
Lac = Lacrimation (sli; mod; sev); Dia = Diarrhea (sli; mod; sev)
Ana = Analgesia, indicated by lack of response to tail pinching
Myd = Mydriasis (sli; mod; sev)
Mot = Altered spontaneous motor activity, either increased (inc) or decreased (dec)
Pil = Piloerection (sli; mod; sev)
Hyp = Hypothermia (sli; mod; sev)

Median Lethal Dose ($LD_{50}$) of AF125

The following are the $LD_{50}$ (95% Confidence Limits) values obtained;
I. Intravenous Injection 68.9 mg./kg. (66.6–71.2)
II. Oral Administration 134.4 mg./kg. (118.4–152.5).

In view of the primary screening results obtained in mice, AF125 appears to possess primarily cholinomimetic activity. It should also be pointed out that with respect to duration of activity, onset of recovery occurred at about 1 to 2 hours after treatment, pending on the dose administered. Particularly under conditions of oral dosing, the comparative onset time of recovery appeared to be relatively rapid. The seemingly narrow ratio between the two respective $LD_{50}$ values, as well as the comparative "active" dose levels after either i.v. or p.os treatment, indicate that AF125 is fairly rapidly absorbed by the enteric route.

AF125(N), AF123

The general pharmacological effects of these compounds are shown in Table 6.

TABLE 6

| Compound | Dose mg/kg | Route of Admin | Mortality | | Major Signs Observed* | | | | | | |
|---|---|---|---|---|---|---|---|---|---|---|---|
| | | | no. | time | Tre | Con | Res | Sal | Myd | Mot | P/H |
| AF125(N) | 100 | i.v. | 5/5 | immed | | | | | | | |
| | 50 | i.v. | 5/5 | immed | | | | | | | |
| | 20 | i.v. | 0/5 | | 3/5 | | 4/5 | sli | sli | dec | |
| | 200 | p.os | 0/5 | | | | | | sli | inc | sli |
| AF123 | 200 | i.v | 5/5 | immed | | | | | | | |
| | 100 | i.v. | 5/5 | 1 min. | | 5/5 | | | | | |
| | 50 | i.v. | 0/5 | | | | | | | | |
| | 400 | p.os | 5/5 | 3 mins. | 5/5 | 5/5 | 5/5 | | | | |
| | 200 | p.os | 0/5 | 3 mins. | 4/5 | | | | | | | r to no. of animals affected out of the total no. of animals treated. For other abbreviations see details above, and additionally:
P/H = Piloerection/Hypothermia (sli; mod; sev)

TEST 4
Improvement of amnesia caused by scopolamine in rats
Step-through Passive Avoidance Test Naive male Sprague-Dawley rats, three months old (obtained from Charles River Breeding, U.K.), were used (weighing 200-300 g.). The passive avoidance (PA) test is according to Fisher et al, Neurosci. Lett. 102: 325 (1989), except that in these rats amnesia was induced by scopolamine.

Eight groups of 17-20 naive rats were used. Each group was divided into two subgroups of 7-10 rats each: subgroup 1 was injected with scopolamine HBr (0.5 mg./kg. in saline, s.c., 15 min. before the shock) and subgroup 2 was injected with saline (1 mg./kg., s.c., 15 min. before the shock). Seven of the groups were treated within one minute after the shock with one of the following doses of the tested compound: 0.1, 0.5, 1, 3, 5, 8, 10 mg./kg. (in saline, i.p.) and one group received saline (1 ml./kg., i.p.).

AF125

The initial latency and retention latency measures were analyzed by a two-way ANOVA (pre-shock scopolamine treatment/post-shock AF125 treatment). Tables 7 and 8 present the means ±S.E.M. of the initial and retention latencies, respectively.

TABLE 7

| Initial latency measures of preshock scopolamine-postshock AF125 treated rats | | | | |
|---|---|---|---|---|
| Post-shock AF125 Dose (mg/kg) | Pre-shock | | | |
| | Saline | | Scopolamine | |
| | Mean | S.E.M. | Mean | S.E.M. |
| Saline | 28.7 | 6.1 | 23.5 | 9.8 |
| 0.1 | 49.5 | 10.9 | 33.6 | 15.8 |
| 0.5 | 42.0 | 9.0 | 47.4 | 19.0 |
| 1.0 | 36.0 | 14.5 | 23.3 | 4.9 |
| 3.0 | 51.9 | 12.9 | 47.3 | 11.8 |
| 5.0 | 34.7 | 11.4 | 51.3 | 14.6 |
| 8.0 | 41.2 | 6.8 | 53.9 | 12.2 |
| 10.0 | 46.3 | 14.0 | 45.9 | 12.6 |

TABLE 8

| Retention latency measure of preshock scopolamine-postshock AF125 treated rats | | | | |
|---|---|---|---|---|
| Post-shock AF125 Dose (mg/kg) | Pre-shock | | | |
| | Saline | | Scopolamine | |
| | Mean | S.E.M. | Mean | S.E.M. |
| Saline | 600.0 | 0.0 | 97.9 | 42.5 |
| 0.1 | 572.8 | 27.2 | 128.8 | 69.4 |
| 0.5 | 600.0 | 0.0 | 222.7 | 76.5 |
| 1.0 | 555.8 | 41.1 | 261.2 | 82.7 |

TABLE 8-continued

Retention latency measure of preshock scopolamine-postshock AF125 treated rats

| Post-shock AF125 Dose (mg/kg) | Pre-shock | | | |
|---|---|---|---|---|
| | Saline | | Scopolamine | |
| | Mean | S.E.M. | Mean | S.E.M. |
| 3.0 | 530.4 | 49.5 | 296.0 | 84.1 |
| 5.0 | 426.7 | 53.4 | 227.3 | 81.4 |
| 8.0 | 594.1 | 6.0 | 294.9 | 98.0 |
| 10.0 | 498.3 | 59.0 | 288.3 | 103.2 |

CONCLUSIONS

The reversal screening experiment using scopolamine as a pre-shock treatment and AF125 as a post-shock treatment yielded a significant dose response curve. The doses of 3, 5, 8 and 10 mg./kg. had an obvious advantage as compared to all other doses. Rats treated with the above doses exhibited the longest retention latencies when compared to the saline treated rats. The lower doses exhibited short retention latencies indicating no improvement in cognitive functions. No significant differences were found in the initial latencies between all the groups tested.

The effect of the post shock AF125 treatment was found significant ($F=104.77$, $df=1/126$, $p<0.001$), 10 mg./kg. ($p<0.05$), increased significantly the retention latency of the scopolamine-treated rats. In addition, AF125 (5 mg./kg.) significantly ($p<0.05$) decreased the retention latency of the pre-shock saline treated rats. Finally, a significant difference was found between the retention latency of the preshock scopolamine/post-shock saline treated rats and the pre-shock saline/post-shock saline treated rats ($p<0.001$). All pre-shock saline treated rats who received AF125 post-shock in the doses: 3, 5, 8 and 10 mg./kg. had side effects.

The group which received 3 mg./kg. had slight diarrhea, the 5 mg./kg. treated group exhibited stronger diarrhea and the 8 and 10 mg./kg. treated groups had severe diarrhea with lacrimation. It is important to note that the pre-shock scopolamine treated rats did not exhibit any side effects following AF125 treatment.

Compared to AF102B (U.S. Pat. No. 4,855,290), AF125 showed a wider dose-response curve; AF102B had a significant enhancing effect on retention-behavior, using the doses of 3 and 5 mg./kg., while the enhancing effect of AF125 continued along a wider range from 3 to 10 mg./kg. All these results would indicate that the beneficial effect of AF125 in this model are due to its potential central agonistic effect on muscarinic receptors which are involved in cognitive functions.

AF125(N)

Subjects

Naive male Sprague-Dawley rats, three months old (obtained from Charles-River Breeding, U.K.), were used (weighing 200–300 g).

Behavioral test

Eight groups of 18–20 naive rats each were used. Each group was divided into two subgroups of 9–10 rata each: subgroup 1 was injected with scopolamine HBr (0.5 mg./kg. in saline, s.c., 15 min. before the shock) and subgroup 2 was injected with saline (1 ml./kg., s.c., 15 min. before the shock). Seven of the groups were treated, within one minute after the shock, with one of the following doses of AF125(N): 0.1, 0.5, 1, 3, 5, 8 or 10 mg./kg. (in saline, i.p.) and one group received saline (1 ml./kg., i.p.).

The initial latency and retention latency measures were analyzed by a two way ANOVA (pre-shock) scopolamine treatment/post-shock AF125(N) (treatment). Tables 10 and 11 present the mean ±S.E.M. of the initial and retention latencies, respectively.

TABLE 10

Initial latency measures of preshock scopolamine-postshock AF125(N) treated rats

| Post-shock AF125N Dose (mg/kg) | Pre-shock | | | |
|---|---|---|---|---|
| | Saline | | Scopolamine | |
| | Mean | S.E.M. | Mean | S.E.M. |
| Saline | 26.7 | 4.7 | 39.1 | 17.6 |
| 0.1 | 21.0 | 2.7 | 22.3 | 5.6 |
| 0.5 | 28.1 | 7.7 | 62.9 | 17.4 |
| 1.0 | 22.0 | 4.2 | 29.1 | 14.5 |
| 3.0 | 44.1 | 14.1 | 23.1 | 4.0 |
| 5.0 | 65.1 | 18.5 | 24.6 | 5.3 |
| 8.0 | 19.3 | 5.4 | 16.3 | 2.7 |
| 10.0 | 14.9 | 2.2 | 21.5 | 5.3 |

A significant difference ($F(7/140)=2.37$, $p<0.05$) in the initial latency was found between the groups treated with AF125(N) (Table 10). An interaction between AF125(N) treatments and the preshock treatment (saline vs scopolamine) was also found ($F(7/140)=22.43$, $p<0.05$). A Scheffee' test showed, more specifically, that the initial latency for the preshock scopolamine-postshock (AF125(N) 0.5 mg./kg. treated rats ($62.9\pm17.4$ sec.) was significantly ($p<0.025$) longer than the initial latency for the control group (preshock scopolamine-postschock saline, $39.1\pm17.6$ sec.). The preshock saline-postshock AF125(N) 5 mg./kg. treated group also had a significantly longer initial latency when compared to the control group: preshock saline-postshock saline treated group ($65.1\pm18.5$ vs $26.7\pm4.7$ sec., $p<0.001$. The effect of the post-shock AF125(N) treatment was found to be significant ($F(7/140)=3.51$, $p<0.05$) and Table 11). A Scheffee' test showed specifically that the dose of 0.5 mg./kg. of AF125(N) increased significantly the retention latency of the scopolamine-treated rats when compared to the saline treated rats ($332.7\pm80.9$ vs $141.1\pm5.5$ sec, $p<0.005$).

TABLE 11

Retention latency measure of preshock scopolamine-postshock AF125(N) treated rats

| Post-shock AF125N Dose (mg/kg) | Pre-shock | | | |
|---|---|---|---|---|
| | saline | | Scopolamine | |
| | Mean | S.E.M. | Mean | S.E.M. |
| Saline | 483.6 | 64.9 | 141.1 | 55.5 |
| 0.1 | 554.7 | 22.5 | 199.7 | 71.7 |
| 0.5 | 600.0 | 0.0 | 332.7* | 80.9 |
| 1.0 | 448.9 | 56.7 | 114.8 | 56.2 |
| 3.0 | 500.1 | 44.0 | 243.4 | 69.2 |
| 5.0 | 290.3 | 52.1 | 181.6 | 58.2 |
| 8.0 | 552.0 | 28.3 | 210.2 | 61.5 |
| 10.0 | 417.5 | 64.9 | 129.7 | 42.2 |

*$p < .005$, compared to saline

In addition, AF125(N) (5 mg./kg., i.p.) significantly decreased the retention latency of the pre-shock saline treated rats when compared to their control group ($290.3\pm52.1$ vs $483.6\pm64.9$ sec., $p<0.005$). Finally, a significant difference was found between the retention latency of the pre-shock scopolamine/post-shock saline treated rats and the pre-shock saline/post-shock saline treated rats ($141.1\pm55.5$ vs $483.6\pm64.9$, $p<0.001$). The treatment with AF125(N) did not cause obvious side effects in any of the doses given either post-scopolamine or post-saline administration. The reversal screening experiment using scopolamine as a pre-shock treatement and AF125(N) as a post-shock treatment yielded a positive significant response only following one dose: 0.5 mg./kg., i.p. Rats treated with this dose exhibited longer retention latency when compared to the saline treated rats.

BEHAVIORAL STUDIES

Test5

AF64A-Injected Animal Model - Morris Water Maze (MWM)

60 Male Sprague-Dawley (raised by Charles River) rats, were used in this experiment. The inter-experiments-interval was 3.5 months. The rats were 7.5 months old and weighed between 310–580 ag at beginning of the experiment.

Drug Administration

30 AF64A (3 nmoles/2 $\mu$l/side, i.c.v.) and 30 saline-injected rats were randomly subdivided into three subgroups: AF125, 1 and 3 mg..kg., i.p., and saline 1 ml./kg., i.p. AF125 and saline were administered once a day for 5 days, 30 min. before testing.

Apparatus and Behavioral Testing

The experiment was performed using a tracking system consisting of an image-analyzer (Cis-2) coupled to a microcomputer (8 MZHz-IBM AT) Galai Laboratories, Ltd.).

Training days

For each rat the escape latency, path-length and swimming speed of the 4 trials in each of the 4 training days were grouped into blocks (one block for each day). The escape-latency, path-length and swimming speed scopres were analyzed by a 3-way ANOVA ($2\times3\times4$) with one repeated variable (Days) and two non-repeated variables (Injection-AF64A/saline and Treatment AF125 1 and 3 mg./kg./saline. In each subgroup the score of one animal was excluded because of extreme deviation from the group average. The statistical analysis included 9 animals for each subgroup.

a. Escape-latency: AF64A-injected rats showed significantly larger escape latencies ($62.5\pm3.0$ sec.), indicating a worse RM performance, than the saline-injected rats ($39.5\pm2.2$ sec.), $[F(1/48)=20.2; p<0.001]$. An interaction between treatment and training days was found $[F(6/144)=3.8; p<0.005]$. In the first day of training the escape latency of AF64A-injected rats, treated with AF125, 1 and 3 mg./kg., was longer than that of AF64A-saline rats ($p<0.001$). During the second and the third days of training AF125 - 1 mg./kg. improved the escape latency of AF64A injected rats ($p<0.001$) while in rats treated with AF125-3 mg.kg. no improvement was found. In the second day of training saline-injected rats treated with AF125 - 3 mg./kg showed a longer escape latency than the AF64A-saline rats ($p<0.05$). A significant general effect of training was shown $[F(3/144)=16.7; p<0.001]$; the escape latency of all groups decreased during the 3 training days ($p<0.05$, by simple effects' contrasts) and stabilized on the fourth day.

b. Path-length: AF64A-injected rats showed a significantly longer path-length, indicating a worse RM performance ($1014.9\pm49.9$ cm) than saline-injected rats ($626.4\pm32.5$ cm)), $[F(1/48)=24.5; p<0.001]$. An interaction between treatment and training days was shown $[F(6/144)=4.3; p<0.001]$: During the second and third day AF64A-injected rats treated with AF125 - 1 mg./kg. improved their path-length compared to AF64A - saline rats ($p<0.001$). In the fourth day of training AF125 - 1 and 3 mg./kg. deteriorated the path-length of AF64A-injected rats compared to AF6-4A-saline rats ($p<0.05$). AF125 3 mg./kg. improved the path length of saline-injected rats in the first day of training but in the second and in the third day it caused deterioration in performance ($p<0.05$). A significant general effect of training was shown ($F(3/144)=11.5$; $p<0.001$]: The path length of all groups significantly decreased during the second to the fourth days of training ($p<0.05$). However, an interaction between injection and training days was found $[F(3/144)=4.1; p<0.01]$: The path-length of AF64A-injected rats decreased only between the second to the third day ($p<0.01$) while in saline/injected rats the path-length decreased during the first 3 days ($P<0.02$).

c. Swimming speed: General effect of training was shown $[F(3/144)=44.8; p<0.001]$; the swimming speed of all groups significantly increased between the first to the second day of training but decreased between the third to the fourth day ($p<0.001$). An interaction between treatment and day of training was shown $[F(6/144)=9.4; p<0.001]$: In AF64A and saline-injected rats treated with AF125 - 1 and 3 mg./kg. the swimming speed in the first day was slower than that of the saline-treated subgroups ($p<0.001$). This effect may partially explain the impairment of learning shown in rats treated with AF125, 1 and 3 mg./kg. in the first day of training.

REVERSAL TEST

For each rat the escape latency and path-length of trails No. 17–21 on the fifth day, were grouped into one block. The scores were analysed by a 2-way ANOVA ($2\times3$) with two variables (Injection-AF64A/saline and Treatment-A125 1 and 3 mg./kg./saline).

a. Escape latency: AF64A-injected rats showed significantly larger escape latencies ($43.9\pm5.9$ sec.) than saline-injected rats ($16.6\pm1.9$ sec.) $[F(1.48); p<0.001]$. In AF64A-injected rats treated with AF125 3 mg./kg. a slight tendency to deteriorate the path-length was found compared to AF64A-saline rats.

b. Path-length: AF64A-injected rats showed a significantly longer path length ($789.3\pm100.0$ cm) than the saline-injected rats ($295.8\pm34.7$ cm) $[F(1/48(=26.2; p<0.001]$. In AF64A-injected rats treated with AF125-3 mg./kg. the path-length was significantly longer than that of the AF64-saline rats ($p<0.05$).

c. Swimming speed: No significant differences were found between any of the groups tested.

Transfer-Trial

No significant spatial bias was found for any of the groups tested in the escape-latency and the path-length measures.

Side effects

All of the AF64A-injected rats, receiving the higher dose of AF125 - 3 mg./kg., were hyperactive. Most of them had also a severe diarrhoea. The AF64A-injected rats which received the lower dose of AF125 - 1 mg./kg. - had only diarrhoea without hyperactivity. The saline-injected rats receiving the higher dose of AF125 had a severe diarrhoea with lacrimation while those receiving the lower dose, 1 mg./kg., had only diarrhoea.

Conclusions

1. AF64A-injected rats showed a significant decrease in acquisition and reversal learning, compared to saline-injected rats.
2. AF125 (1 mg./kg., i.p.) improved acquisition of the platform-location in AF64F-injected rats during both the second and third days of training. However, this compound, in both 1 and 3 mg./kg. doses, impaired the performance of those rats during the first day of training. Furthermore, the path-length measure showed a deterioration of performance also on the fourth day.
3. Impairment of performance of the AF64A-injected rats by AF125 (2 and 3 mg./kg.) on the first day of training may be partially explained by an impairment in their motor coordinative ability. The swimming speed of both groups was significantly slower than that of AF64A-saline rats on that day. However, such motor coordinative deficiency was not found on the fourth day of training; therefore, the deterioration in performance of both groups on that day might be due to a high dose.
4. AF125 had no beneficial effect on reversal-learning of AF64A-injected rats.

TEST 6

AF64A - Injected Animal Model - 8-arm radial maze (RAM) Introduction

In the present study the potential effect of AF125 in reversing memory deficits was evaluated on the performance of AF64-injected mature rats, in the RAM. One of the suggestions raised following the MWM experiment with this compound was its reappraisal using a lower dose. As a result a 0.5 mg./kg. dose of AF125 was used in this study.

METHODS (a) Subjects

Forty eight mature male (11–12 months) rats which were tested in the MWM were used in this study. There were injected icv with AF64A 8 months earlier, at the age of three months. One week before the behavioral testing, rats were transferred to individual cages and were food restricted until reaching 90% of their free feeding weight (the rats had free access to water). The room was illuminated 12 hrs a day (6:00 to 18:00) and behavioral testing sessions were carried out during the mornings. After reaching 90% of free feeding weight, rats received about 4 food pellets per day (Altromin, 15 g.) in order to further reduce the rats' weights. Two days before behavioral testing the rats were fed with precision pellets (Bioserv Inc.) which were later used for reinforcement in the maze.

(b) Apparatus

Behavioral tests were conducted in an elevated (70 cm) 8-arms radial maze, made of PVC. The arms (75 cm long and 10 cm wide) extended from an octagonal central arena (40 cm wide). At the end of each arm a self feeder was placed (45 mg pellet dispenser Model 8000. (Lafayette Instrument Company).

(c) Behavioral testing (1) Pretraining

Before starting the actual test the rats were familiarized with the RAM. Pellets were scattered in the whole area of the maze. Rats were placed in the central arena, one at a time, facing always the same direction, and were permitted to run from arm to arm until visiting all 8 arms or until 10 minutes had elapsed. Pretraining lasted two weeks (five days a week).

(2) Training

Due to the size of the batch (48 rats) the experiment was conducted in two phases. Twelve AF64A-injected rats and 12 saline-injected rats participated in each phase. The rats were randomly assigned to the different phases. The rats in each phase were further divided into two subgroups - drug treated and controls. In each of the training days each rat was placed in the central arena 30 minutes following injection of either AF125 (0.5 mg./kg. solution in saline, i.p.) or saline 1 mg./kg., i.p.). The rats were allowed to run from arm to arm until 8 pellets were collected or until 15 minutes had elapsed. For each rat the correct choices, number of errors and total time of the five training days were grouped into 1 block. The correct choices, number of errors and total time scores were analyzed by a 2-way ANOVA (2×2) (Injection-AF64A/saline and Treatment-AF125 0.5 mg./kg./saline.

Correct Choices

A significant difference was found in the average number of correct choices out of the first eight entries between the AF64A-injected rats' performance (6.0±0.24) and that of the saline-injected rats (6.8±0.15) ($F(1/36)=9.29$, $p<0.005$). In addition a significant interaction between injection and treatment was found ($F(1/36)=6.35$, $p<0.025$). Scheffe' tests showed that AF125 improved the performance of the AF64A-injected rats (6.53±0.36) compared to that of the saline treated rats (5.49±0.26), ($p<0.025$). Furthermore no significant difference was found between the performance of the AF64A-injected rats treated with AF125 and that of saline-injected rats treated with saline.

Number of errors

The AF64A-injected rats made significantly more errors (7.69±1.1) than the saline-injected rats (3.5±0.59) ($F=(1/36)=10.11$, $p<0.001$). AF125 treatment did not have any effect on this parameter.

Total time

No significant difference was found between any of the groups in the total time measure.

Body weight

Comparing the mean weights of the rats before behavioral testing by a t-test revealed an overall significant difference ($t=(38)=4.05$, $p<0.001$) between the AF64A-injected rats (489.5 g.) and the saline injected rats (579 g.). The effect of AF125 on the body weights was not tested because rats were food restricted.

Side-effects

The dose of 0.5 mg./kg. used in this study caused less side-effects than the higher doses (1 and 3 mg./kg.) which were used in the MWM experiment. Only two saline-injected rats treated with AF125 had diarrhoea. Other side-effects were not found.

CONCLUSIONS

1. AF64A-injected rats showed a significant decrease in performance which was expressed in both parameters: number of correct choices out of the first eight entries and number of errors.

2. AF125 (0.5 mg./kg., i.p.) significantly improved the performance of AF64A injected rats. This result was illustrated only by the parameter of correct out of the first eight entries.

3. The side-effects of the test-compound AF125 were minimal probably because of the low dose—0.5 mg./kg., compared to the higher doses (1 and 3 mg./kg.) used in the MWM experiment.

TEST 7

Stimulation of phosphpoinositides hydrolysis in SK-N-SH cells by AF125

The new compound AF125 was assayed for its ability to stimulate phosphoinositide hydrolysis in cultured human neuroblastoma cells, line SK-N-SH (using the method of Stein et al, 1988 EMBO J. 7: 30331–3035). These cells express the $m_3$ muscarinic cholinergic receptor subtype, which is coupled to phosphoinositides hydrolysis, but not the $m_1$ subtype (Pinkas-Kramarski et al, Neuroscience Lett. 1990, 108; 335–340; Luthin et al Mol. Pharmacol. 1988, 34: 327–333; Baumgold and White, Biochem. Pharmacol. 1989, 38: 1605).

In a typical experiment, the accumulation of inositol-1-phosphate (IP) was stimulated 7.46-fold over basal level by 10 mM carbachol, 5./24-fold by 1 mM oxotremorine-M, and 1.42-fold by 1 mM AF125. In contrast, the M1-selective agonist AF102B (U.S. Pat. No. 4,855,290) failed to stimulate phosphoinositide hydrolysis in these cells even at 1 mM, while at that concentration it could completely block the oxotremorine-M-induced signal. This inhibition was dependent on oxotremorine-M concentration; for example, 1 mM AF102B completely blocked phosphoinositide hydrolysis induced by 10 μM oxotremorine-M while inhibiting the signal of 1 mM oxotremorine-M by 34%.

In addition, the combined stimulation of phosphoinositides hydrolysis by carbachol and the new compounds was checked: in the same experiment, the accumulation of $IP_1$ was stimulated 6.11-fold over basal level by a combination of mM carbachol with 1 mM AF125. Hence, the new compound AF125 stimulates phosphoinositides hydrolylsis in SK-N-SH human neuroblastoma cells to about 20-25% of the stimulation obtained with the non-selective full agonist cabachol, while only minimally (10-20%) interfering with the effect of carbachol.

The significance of these results is that AF125 shows a unique activity as a muscarinic agonist in this cell line which expresses mainly $m_3$ muscarinic receptor subtype. Thus, this compound could be particularly useful for the treatment of SDAT (Braan et al, FEBS Lett. 230: 90–94, 1988).

While certain embodiments of the invention have been particularly described, it will be apparent to those skilled in the art that many modifications and variations may be made. The invention is accordingly not to be construed as restricted to such embodiments, rather its concept, scope and spirit are to be understood having regard to the claims which follow.

We claim:

1. A compound of formula (I)

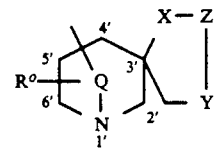

including enantiomers, racemates and acid addition and quaternary salts thereof, wherein one of X and Y is O and the other of X and Y is N; Q is a member selected from the group consisting of $(CH_2)_n$ and $C(CH_3)_2$ where n is 1, 2 or 3 and the bridge —Q— is attached at one end to position 1 and at the other end to position 4 or 5, and R° is selected from the group consisting of hydrogen, methyl and hydroxyl; the moiety

denotes a member selected from the group consisting of sub-groups (a) and (b), in which the line connecting Z and Y signifies the presence of a double bond in sub-group (a) when X—Z is O—C—R and Y is N, the presence of a single bond in sub-group (a) when X—Z is N═C═R and Y is O, and the absence of a bond in sub-group (b) and in which: in sub-group (a) Z is C—R wherein R is selected from the group consisting of hydrogen, $NH_2$, NH—$C_{1-6}$-alkyl, N($C_{1-6}$-alkyl)$_2$, $C_{1-6}$-alkyl, $C_{2-6}$-alkenyl, $C_{2-6}$alkynyl, $C_{3-7}$-cycloalkyl, $C_{1-6}$-alkyl substituted by 1-6 halogen atoms, hydroxy-$C_{1-6}$-alkyl, $C_{1-6}$-alkoxy-$C_{1-6}$-alkyl, carboxyl-$C_{1-6}$-alkyl, ($C_{1-6}$-alkoxy)carbonyl-$C_{1-6}$-alkyl, amino-$C_{1-6}$-alkyl, mono-($C_{1-6}$-alkyl)amino-$C_{1-6}$-alkyl, di-($C_{1-6}$-alkyl)amino-$C_{1-6}$-alkyl, 2-oxo pyrrolidin-1-ylmethyl, aryl, diarylmethylol, and $C_{1-6}$-alkyl substituted by one or two aryl groups, wherein aryl denotes unsubstituted phenyl or phenyl substituted by 1-3 substituents selected from the group consisting of halogen, $C_{1-6}$-alkyl, $C_{1-6}$-alkoxy and $CF_3$; and in sub-group (b) X is O, Z is H and Y is selected from the group consisting of $NH_2$, $NO_2$ and $N_3$ excluding 3-aminomethylquinuclidin-3-ol.

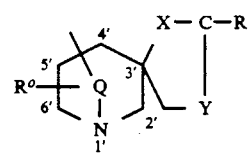

including enantiomers, racemates and acid addition and quaternary salts thereof, wherein one of X and Y is O and the other of X and Y is N; Q is a member selected from the group consisting of $(CH_2)_n$ and $C(CH_3)_2$ where n is 1, 2 or 3 and the bridge —Q— is attached at one end to position 1 and at the other end to position 4 or 5, and R° is selected from the group consisting of hydrogen, methyl and hydroxy; in the moiety

the line connecting C—R and Y signifies the presence of a double bond when X is O and Y is N, and the presence of a single bond when X is N— and Y is O; and in C—R, R is selected from the group consisting of hydrogen, NH$_2$, NH-C$_{1-6}$-alkyl, N(C$_{1-6}$-alkyl)$_2$, C$_{1-6}$-alkyl, C$_{2-6}$-alkenyl, C$_{2-6}$-alkynyl, C$_{3-7}$-cycloalkyl, C$_{1-6}$-alkyl substituted by 1-6 halogen atoms, hydroxy-C$_{1-6}$-alkyl, C$_{1-6}$-alkoxy-C$_{1-6}$-alkyl, carboxy-C$_{1-6}$-alkyl, (C$_{1-6}$-alkoxy)carbonyl-C$_{1-6}$-alkyl, amino-C$_{1-6}$-alkyl, mono-(C$_{1-6}$-alkyl)amino-C$_{1-6}$-alkyl, di-(C$_{1-6}$-alkyl)amino-C$_{1-6}$-alkyl, 2-oxo-pyrrolidin-1-ylmethyl, aryl, diarylmethylol, and C$_{1-6}$-alkyl substituted by one or two aryl groups, wherein aryl denotes unsubstituted phenyl and phenyl substituted by 1-3 substituents selected from the group consisting of halogen, C$_{1-6}$-alkyl, C$_{1-6}$-alkoxy and CF$_3$.

3. A compound according to claim 2, wherein n is 2.

4. A compound according to claim 3, wherein R is selected from the group consisting of hydrogen, NH$_2$, NH-C$_{1-6}$-alkyl, N(C$_{1-6}$-alkyl)$_2$, C$_{1-6}$-alkyl and aryl.

5. A compound according to claim 4, which is selected from the group consisting of:
2-aminospiro(1,3-oxazoline-5,3')quinuclidine,
2-methylspiro(1,3oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and acid addition and quaternary salts thereof.

6. A compound according to claim 1, which is selected from the group consisting of 3-nitromethylquinuclidin-3-ol and 3-azidomethylquinuclidin-3-ol.

7. A pharmaceutical composition for use in treating diseases of the central and peripheral nervous system in mammals, which comprises an amount effective for use in treating said diseases, of at least one member of the group consisting of compounds of the formula (I) as defined in claim 2, including enantiomers, racemates and pharmaceutically compatible addition and quaternary salts thereof, together with an inert carrier or diluent.

8. A pharmaceutical composition according to claim 7, which is in a form suitable for oral, rectal, parenteral or transdermal administration, or for administration by insufflation or nasal spray.

9. A pharmaceutical composition according to claim 8, which is in a form suitable for transdermal administration and which comprises as an additional component, a low molecular weight fatty acid.

10. A pharmaceutical composition according to claim 8, which is in unit dosage form.

11. A pharmaceutical composition according to claim 10, wherein said at least one member is present in an amount in the range of about 0.5 to about 100 mg., together with an inert carrier or diluent.

12. A pharmaceutical composition according to claim 11, wherein said amount lies within the range of about 5 to about 100 mg.

13. A pharmaceutical composition according to claim 12, wherein said amount lines within the range of about 10 to about 50 mg.

14. A pharmaceutical composition according to claim 7, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinculidine, including enantiomers, racemates and pharmaceutically compatible acid addition and quaternary salts thereof.

15. A pharmaceutical composition for use in treating diseases of the central and peripheral nervous system mammals, which comprises an amount effective for use in treating said diseases, of at least one member of the group consisting of compounds of the formula (I) as defined in claim 2, including enantiomers, racemates and pharmaceutically compatible addition and quaternary salts thereof, and at least one compound selected from the group consisting of physostigmine, tetrahydroaminoacridine, choline, lecithin, piracetam, aniracetam, pramiracetam, oxiracetam, 4-aminopyridie, 3,4-diaminopyridine, somatostatin pirenzepine, N-methylatropine, N-butylscopolamime, scopolamine, clonidine, quanfamicine, propantheline, methantheline, glycopyroolate, tropenzilium, nortriptyline, amitriptyline, imipramine, minaprine, secoverine, AFDX-116, nicotine, alaproclate, zimelidine, deprenyl and Nerve Growth Factor.

16. A pharmaceutical composition to claim 15, which is in a form suitable for oral, rectal, parenteral or transdermal administration, or for administration by insufflation or nasal spray.

17. A pharmaceutical composition according to claim 16, which is in a form suitable for transdermal administration and which comprises as an additional component, a low molecular weight fatty acid.

18. A pharmaceutical composition according to claim 16, which is in unit dosage form.

19. A pharmaceutical composition according to claim 18, wherein said at least one member is present in an amount in the range of about 0.5 to about 100 mg., together with an inert carrier or diluent.

20. A pharmaceutical composition according to claim 19, wherein said amount lies within the range of about 5 to about 100 mg.

21. A pharmaceutical composition according to claim 20, wherein said amount lies within the range of about 10 to about 50 mg.

22. A pharmaceutical composition according to claim 15, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and pharmaceutically compatible acid addition and quarternary salts thereof.

23. A pharmaceutical composition according to claim 15 and which also comprises an inert carrier or diluent.

24. A method for treating diseases of the central and peripheral nervous system in mammals, which comprises administering to the mammal an amount effective for use in treating said diseases, of at least one member of the group consisting of compounds of the formula (I) as defined in claim 2, including enantiomers, racemates and pharmaceutically compatible acid addition and quaternary salts thereof.

25. A method according to claim 24, wherein said at least one member is in the form of a pharmaceutical composition which comprises an inert carrier or diluent.

26. A method according to claim 25, wherein said pharmaceutical composition is in a form suitable for oral, rectal, parenteral or transdermal administration, or for administration by insufflation or nasal spray.

27. A method according to claim 26, wherein said pharmaceutical composition is in a form suitable for transdermal administration and which comprises as an additional component, a low molecular weight fatty acid.

28. A method according to claim 26, wherein said pharmaceutical composition is in unit dosage form.

29. A method according to claim 28, wherein in said pharmaceutical composition, wherein said at least one member is present in an amount in the range of about 0.5 to about 100 mg.

30. A method according to claim 29, wherein said amount lies within the range of about 5 to about 100 mg.

31. A method according to claim 30, wherein said amount lies within the range of about 10 to about 50 mg.

32. A method according to claim 24, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and pharmaceutically compatible acid addition and quaternary salts thereof.

33. A method according to claim 25, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and pharmaceutically compatible acid addition and quaternary salts thereof.

34. A method for treating diseases of the central and peripheral nervous system in mammals, which comprises administering to the mammal an amount effective for use in treating said diseases, of at least one member of the group consisting of compounds of the formula (I) as defined in claim 2, including enantiomers, racemates and pharmaceutically compatible addition and quaternary salts thereof, and at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine, propantheline, methantheline, glycopyrrolate, tropenzilium, nortriptyline, amitriptyline, imipramine, minaprine, secoverine, AFDX-116, nicotine, alaproclate, zimelidine, deprenyl and Nerve Growth Factor.

35. A method according to claim 34, wherein both said at least one member and said at least one compound are administered in the form of a pharmaceutical composition which comprises an inert carrier or diluent.

36. A method according to claim 35, wherein said pharmaceutical composition is in a form suitable for oral, rectal, parenteral or transdermal administration, or for administration by insufflation or nasal spray.

37. A method according to claim 36, wherein said pharmaceutical composition is in a form suitable for transdermal administration and which comprises as an additional component, a low molecular weight fatty acid.

38. A method according to claim 36, wherein said pharmaceutical composition is in unit dosage form.

39. A method according to claim 38, wherein in said pharmaceutical composition, wherein said at least one member is present in an amount in the range of about 0.5 to about 100 mg.

40. A method according to claim 39, wherein said amount lies within the range of about 5 to about 100 mg.

41. A method according to claim 40, wherein said amount lies within the range of about 10 to about 50 mg.

42. A method according to claim 34, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and pharmaceutically compatible acid addition and quaternary salts thereof.

43. A method according to claim 35, wherein said at least one member is selected from the group consisting of:
2-aminospiro(1,3-oxazoline-5,3')quinuclidine,
2-methylspiro(1,3-oxazoline-5,3')quinuclidine,
2-ethylspiro(1,3-oxazoline-5,3')quinuclidine,
2-phenylspiro(1,3-oxazoline-5,3')quinuclidine, including enantiomers, racemates and pharmaceutically compatible acid addition and quaternary salts thereof.

44. A method as in claim 24, wherein there are treated diseases due to a deficiency in the central cholinergic system.

45. A method as in claim 44, wherein there is treated senile dementia of Alzheimer's type.

46. A method as in claim 45, wherein said at least one member is administered via the oral route in an amount which lies within the range of about 0.1 to about 60 mg./kg. body weight.

47. A method as in claim 46, wherein said amount lies within the range of about 0.1 to about 10 mg./kg. body weight.

48. A method as in claim 47 wherein said amount lies within the range of about 1 to about 5 mg./kg. body weight.

49. A method as in claim 44, wherein there is also coadministered with the said quinuclidine, at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine, propantheline, methantheline, glycopyrrolate, tropenzilium, nortriptyline, amitriptyline, imipramine, minaprine, secoverine, AFDX-116, nicotine, alaproclate, zimelidine, deprenyl and Nerve Growth Factor.

50. A method as in claim 45, wherein said at least one member is administered via the parenteral route in an amount which lies within the range of about 0.01 to about 10 mg./kg. body weight.

51. A method as in claim 50, wherein said amount lies within the range of about 0.05 to about 5 mg./kg. body weight.

52. A method according to claim 51 wherein said amount lies within the range of about 0.1 to about 2 mg./kg. body weight.

* * * * *

UNITED STATES PATENT AND TRADEMARK OFFICE
CERTIFICATE OF CORRECTION

PATENT NO. : 5,053,412
DATED : October 1, 1991
INVENTOR(S) : Abraham FISHER and Ishai KARTON It is certified that error appears in the above-indentified patent and that said Letters Patent is hereby corrected as shown below:

Claim 2, column 24, line 44, insert --2. A compound of formula (I')--.

Signed and Sealed this

Second Day of January, 1996

Attest:

BRUCE LEHMAN

Attesting Officer    Commissioner of Patents and Trademarks